United States Patent [19]

Fischell et al.

[11] Patent Number: 5,413,561
[45] Date of Patent: May 9, 1995

[54] GUIDING CATHETER WITH SEALING CAP SYSTEM FOR REDUCING BLOOD LOSS WHEN INSERTING GUIDING CATHETERS

[75] Inventors: Robert E. Fischell, Dayton, Md.; Tim A. Fischell, Nashville, Tenn.

[73] Assignee: Cathco, Inc., Dayton, Md.

[21] Appl. No.: 60,656

[22] Filed: May 13, 1993

[51] Int. Cl.[6] ............................................. A61M 5/178
[52] U.S. Cl. .................................... 604/167; 604/256
[58] Field of Search ............... 604/164, 167, 263, 264, 604/256, 283

[56] References Cited

U.S. PATENT DOCUMENTS

| | | | |
|---|---|---|---|
| 3,513,849 | 5/1970 | Vaillancourt et al. | 604/283 |
| 3,741,217 | 6/1973 | Clarico | 604/283 |
| 4,417,890 | 11/1983 | Dennehey et al. | 604/284 |
| 4,430,081 | 2/1984 | Timmermans | 604/167 |
| 4,722,344 | 2/1988 | Cambros et al. | 128/658 |
| 4,786,281 | 11/1988 | Valentine et al. | 604/167 |
| 4,886,507 | 12/1989 | Patton et al. | 604/284 |
| 4,935,010 | 6/1990 | Cox et al. | 604/167 |
| 4,995,872 | 2/1991 | Ferrara | 604/280 |
| 5,106,054 | 4/1992 | Mollenauer et al. | 251/149.1 |
| 5,114,408 | 5/1992 | Fleischhaker et al. | 604/167 |
| 5,167,644 | 12/1992 | Fischell et al. | 604/264 |
| 5,184,610 | 2/1993 | Martin et al. | 604/284 |
| 5,228,452 | 7/1993 | Samson | 128/772 |
| 5,242,393 | 9/1993 | Brimhall et al. | 604/283 |

FOREIGN PATENT DOCUMENTS 037072081 3/1993 European Pat. Off. .... A61M 25/01
9112840 9/1991 WIPO ........................... 604/284

OTHER PUBLICATIONS

M. I. Canedo, "Tampa Bay Catheter: A New Guiding Catheter for Endomyocardial Biopsy etc." 20 May 1991.
Collection of private corporate papers from The Cordis Corporation.
P. 24 from catalog "OEM Medical Devices and Components:" Medical Disposables Intl. Inc.

Primary Examiner—John G. Weiss

[57] ABSTRACT

The invention is a system for reducing blood loss when placing a guiding catheter into an artery of a human subject. The system consists of a guiding catheter, a sealing means to be placed on the guiding catheter's proximal end and a guide wire that can be placed through both the guiding catheter and the sealing means to assist in placing the guiding catheter into a specific artery. The sealing means is typically a cap consisting of a male Luer lock fitting that includes a hemostasis valve that is designed to seal around the guide wire. The cap can be a separate component or it can be joined to the guiding catheter's proximal end by means of a flexible hinge. After the guiding catheter has been placed at a desired location in the arterial system, the cap and guide wire can be removed and a "Y" adaptor would then be placed onto the guiding catheter's proximal end. If desired the flexible hinge could also be removed from the guiding catheter.

14 Claims, 3 Drawing Sheets

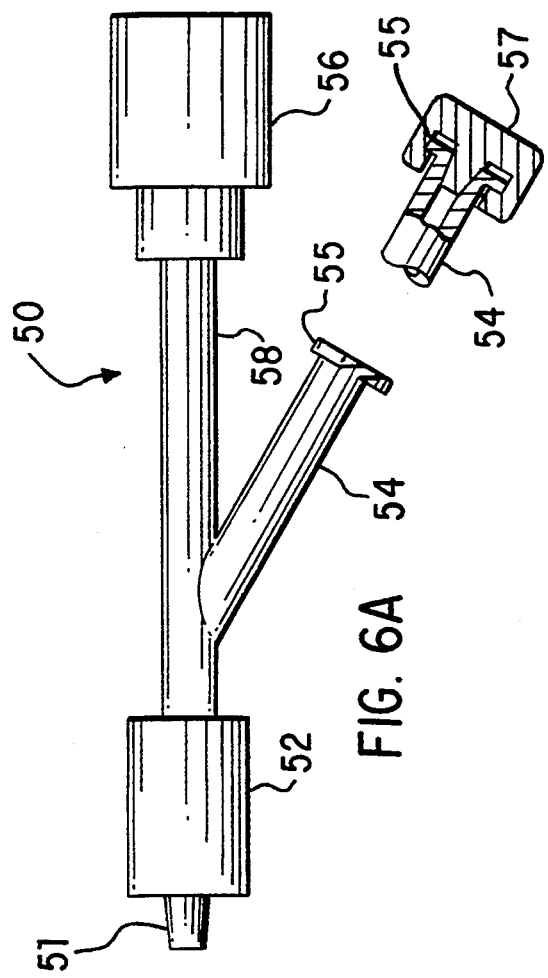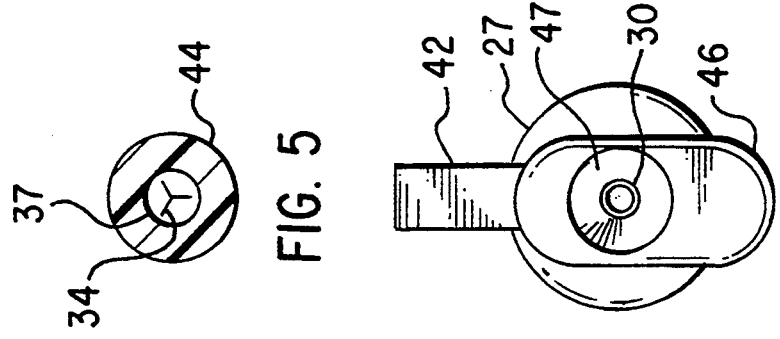

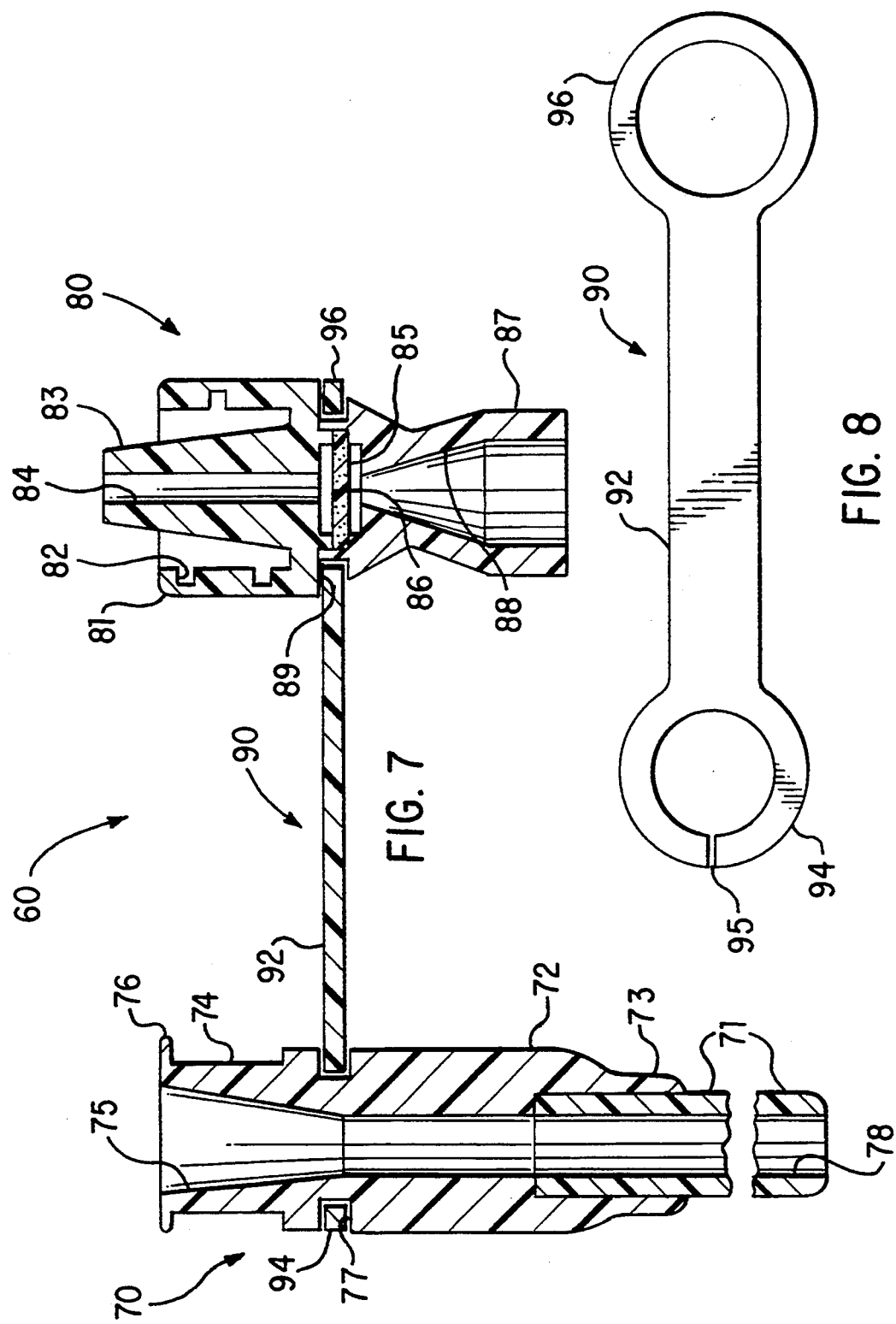

GUIDING CATHETER WITH SEALING CAP SYSTEM FOR REDUCING BLOOD LOSS WHEN INSERTING GUIDING CATHETERS

FIELD OF USE

This invention is in the field of percutaneous guiding catheters that are inserted through a patient's skin in order to facilitate the entry of guide wires and catheters into a blood vessel.

BACKGROUND

Guiding catheters are typically inserted at the groin with their proximal end remaining outside the patient and their distal end placed in an artery. Guide wires are used to help place these guiding catheters at an appropriate place in the arterial system. However, during the time it takes to properly advance the guiding catheter's distal end into the ascending aorta or other large artery, there is typically substantial blood leakage out of the guiding catheter's proximal end. This exposes health care workers to the risks associated with bloodborne pathogens.

U.S. Pat. No. 5,167,644 entitled "Manually Sealable Introducer Sheath" which issued on Dec. 1, 1992 to the present inventors, Robert E. and Tim A. Fischell, describes a similar invention as used with an introducer sheath instead of a guiding catheter which invention is also a means to prevent substantial blood leakage. One difference between the present invention and the invention described in the above referenced U.S. Patent 5,167,644 is that a sheath has a hemostasis valve at its proximal end but a guiding catheter has no means whatsoever to prevent substantial blood leakage.

SUMMARY OF THE INVENTION

The purpose of this invention is to overcome the problem of substantial blood leakage when a guiding catheter is advanced over a guide wire and through the arterial system. The invention consists of a manually placed sealing means or sealing cap that is molded onto or otherwise joined to a section of the guiding catheter near its proximal end. The sealing means has a tapered, conically shaped stopper which can be part of a male Luer lock fitting which is designed to be inserted into the conically shaped, female Luer entry lumen of the guiding catheter. The stopper is flexibly attached to the guiding catheter by a hinged section formed from a thin flexible piece of plastic. Outward from the stopper there can be a stiffened lift section having a greater thickness of plastic as compared to the hinged section.

After the guiding catheter is flushed through its central lumen with a flushing solution such as normal saline, the stopper of the sealing means can be pushed into the Luer lumen or screwed onto the Luer lock fitting at the guiding catheter's proximal end. A guide wire to be used for advancing the guiding catheter into the ascending aorta is then placed through a central lumen in the stopper. The guiding catheter and guide wire are then advanced together through a sheath in the groin until their distal ends lie within the ascending aorta.

The guide wire is then removed, the sealing means is manually opened (i.e., the stopper is pulled out of the guiding catheter's Luer lumen or unscrewed from the Luer lock fitting) and a Tuohy-Borst "Y" adaptor is then promptly placed onto the female Luer lock fitting at the guiding catheter's proximal end. There may be a small amount of blood loss in the one to three seconds from the time the sealing means is opened until the "Y" adaptor is attached, but such loss of blood is extremely slight compared to the amount that is presently lost during the time normally required for guiding catheter placement. It should be noted that it is desireable to leave some flushing fluid within the guiding catheter's lumen so as to increase the time that elapses after the cap is removed and before the "Y" adaptor seals off the guiding catheter's proximal end. With the "Y" adaptor attached at its proximal end, the guiding catheter's distal end is then placed in the ostium of a coronary artery. A similar method is to keep the sealing means on the guiding catheter's proximal end while placing the distal end in the ostium of a coronary artery and then replacing the sealing means with a "Y" adaptor.

Thus it is an object of this invention to provide a means and method to prevent substantial loss of the patient's blood when a guiding catheter is being advanced into the arterial system.

Another object of this invention is to reduce the exposure of health care workers to the patient's bood.

Still another object of this invention is to provide a guiding catheter with a sealing cap wherein a stopper can be manually placed into the Luer lumen at the guiding catheter's proximal end; the stopper being adapted to allow the passage of a guide wire while preventing the free release of blood.

Still another object of this invention is to have the sealing cap attached to the guiding catheter near its proximal end.

Still another object of this invention is to be able to easily remove the sealing cap from the guiding catheter after the guiding catheter has been properly placed within an artery.

These and other objects and advantages of this invention will become obvious to persons of ordinary skill in this art upon reading of the detailed description of the invention presented herein in conjunction with the related drawings.

BRIEF DESCRIPTION OF THE DRAWINGS

FIG. 4 is a top view of the guiding catheter with sealing cap in the closed state.

FIG. 5 is a transverse cross section of the sealing cap at section 5—5 of FIG. 1 which cross section illustrates a hemostasis valve.

FIG. 6A is a side view of a Tuohy-Borst "Y" adaptor.

FIG. 6B shows the cross section of a second sealing means on a separate branch of the "Y" adaptor.

FIG. 7 is a longitudinal cross section of another embodiment of the present invention showing a guiding catheter with a strain relief proximal fitting which is joined by a flexible hinge to a male Luer lock sealing means.

FIG. 8 is a plan view of the flexible hinge.

DETAILED DESCRIPTION OF THE INVENTION

Figure 1:
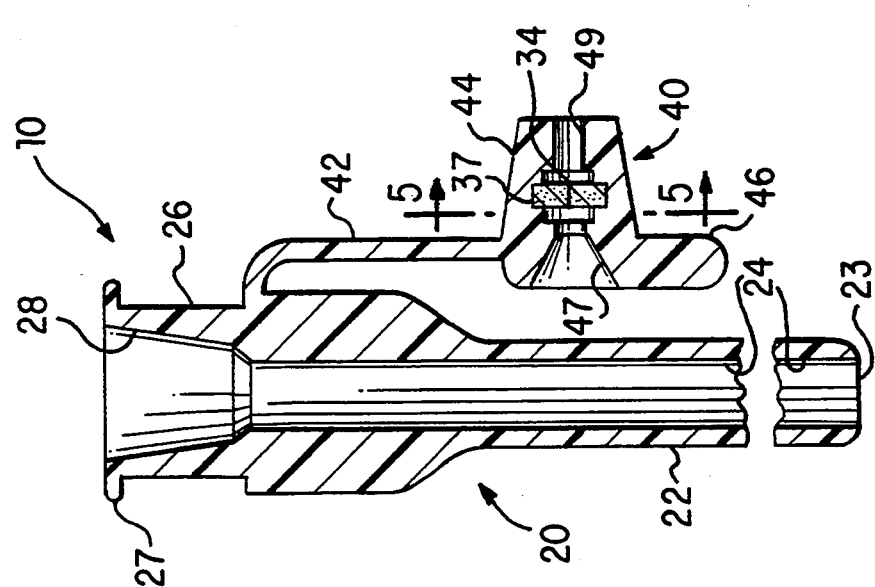
FIG. 1 is a longitudinal cross-sectional view of the guiding catheter with sealing cap shown in the open (unsealed) state.

FIG. 1 is a longitudinal cross-sectional view of the guiding catheter with sealing cap system 10 having a guiding catheter sealing cap 40 attached near the proximal end of the guiding catheter's main body 20. The main body 20 consists of an elongated flexible tube 22 having a central lumen 24, a distal end 23 and a proximal end having a female Luer lock fitting 26 with a thread 27. The Luer fitting 26 has a tapered Luer entry lumen 28 which is designed to mate with a male Luer lock fitting of a Tuohy-Borst "Y" adaptor such as the one shown in FIG. 6.

Figure 2:
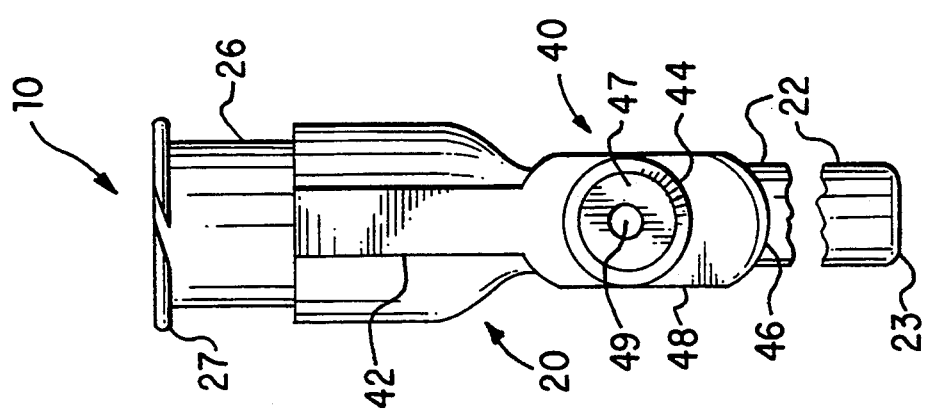
FIG. 2 is a side view of the guiding catheter with sealing cap in the open state.

As shown in FIG. 1, the sealing cap 40 includes a hinge 42 that is molded onto or otherwise attached to the guiding catheter 20. At the center of the cap 40 is a tapered stopper 44 onto which is molded a stiffened section 46. As seen in FIGS. 1 and 5, within the stopper 44 is a soft elastomer hemostasis valve 37 having slits 34. FIG. 2 is a side view of the system 10 which shows a flattened side 48 of the cap 40. Both FIGS. 1 and 2 show that the stopper 44 has a conical entry lumen 47 which then goes into a generally cylindrical lumen 49 through which a guide wire can be passed.

Figure 3:
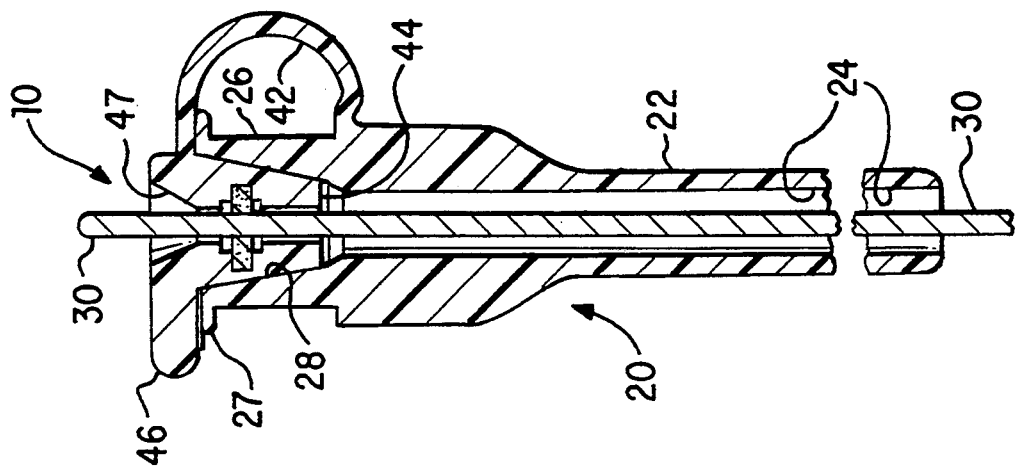
FIG. 3 is a longitudinal cross-sectional view of the guiding catheter with sealing cap shown in its closed (sealed) state.

The cap 40 can be manually placed onto the guiding catheter's main body 20 by bending the flexible hinge 42 so that the stopper 44 is placed within the lumen 28 as shown in FIGS. 3 and 4. When this is done, a guide wire 30 can be placed through the conical lumen 47 and cylindrical lumen 49 of the stopper 44 and the slit 34 of the hemostasis valve 37. In this closed position, the guiding catheter 10 is sealed so that there will not be any significant blood leakage when the guiding catheter 10 and the guide wire 30 are advanced into the arterial system. The lumen 49 would typically be 0.040 inch diameter for a typical 0.038 inch diameter guide wire. This design permits the guide wire 30 to be advanced or pulled back without significant blood leakage. The lumen 49 could be designed without the elastic member 37 as shown in FIG. 1 but with a hole that forms a snug sliding fit around the guide wire 30 but which still allows the guide wire 30 to be free to be advanced or pulled back.

After the distal end 23 of the guiding catheter body 20 is situated in the ascending aorta, the thickened section 46 can be used to pull the stopper 44 out of the Luer lumen 28. The preformed shape of the hinge 42 will then cause the cap 40 to return to its normal position as shown in FIG. 1. In this position, the cap 40 is out of the way so that the "Y" adaptor can be quickly attached to the guiding catheter's proximal end.

The guiding catheter body 20 including the cap 40 would typically be molded from a plastic such as PVC, polyurethane, polyethylene or an equivalent elastomer material. The hemostasis valve 37 would typically be made from a soft elastomer such as silicone or latex rubber.

Although the design described herein is considered to be a preferred embodiment of the invention, it is also anticipated that the hinge 42 may be extended at any angle between 0° and 180° from the guiding catheter body 20.

Another embodiment envisions a separate stopper which is not physically attached to the guiding catheter 65 but could be inserted into or pulled out of the Luer lumen 28. Such a separate stopper could advantageously be of a generally cylindrical shape (with a conical stopper) as opposed to having a flat side such as the flat side 48 shown for the embodiment of FIGS. 1, 2, 3, and 4. It is also conceived that the hinge 42 could be joined with a sliding or elastic attachment onto the guiding catheter's proximal end. It is further conceived that this guiding catheter with cap design as described herein can be placed in other arteries such as the renal or carotid arteries. Furthermore, this sealing cap could be used with diagnostic as well as therapeutic catheters. Still further, the sealing cap could be placed on and could seal against the exterior surface at the guiding catheter's proximal end instead of sealing within the guiding catheter's female Luer lock lumen.

It is also conceivable that the "Y" adaptor as seen in FIG. 6A could be used for the purpose of sealing the proximal end of the guiding catheter while advancing a guide wire through the "Y" adaptor and guiding catheter. Specifically, the "Y" adaptor 50 has at its distal end a male Luer cone 51 which mates with the female entry lumen 28 of the guiding catheter body 20 of FIG. 1. Also, the nut 52 is adapted to engage the Luer thread 27 of the guiding catheter 10. A first branch 54 of the "Y" adaptor has a Luer thread 55 at its open, female Luer fitting end. A second branch 58 leads to a Tuohy-Borst fitting 58 which can provide a seal around a guide wire or the shaft of an artery opening catheter.

The "Y" adaptor could be used for sealing the proximal opening of the guiding catheter body 20 if a closed male Luer lock cap 57 as shown in FIG. 6B is screwed onto the threads 55 of the first branch 54 and the guide wire is advanced through the Tuohy-Borst fitting 58 after it has been adjusted to allow a snug sliding fit onto the guide wire. Also, the Tuohy-Borst fitting 58 could be tightly closed and a male Luer fitting with a hemostasis valve could be joined to the first branch 54 of the "Y" adapter 50, and a guide wire advanced through the hemostasis valve and it into the guiding catheter.

A guiding catheter with sealing cap system 60 shown in FIG. 7 is an alternative embodiment of the present invention. The system 60 consists of a guiding catheter 70, a male Luer lock sealing cap 80 and a flexible hinge 90. The guiding catheter 70 has an elongated, generally cylindrical main body 71 with a central lumen 78. Molded onto the body 71 is a proximal strain relief fitting 72 having a female Luer lock fitting 74 at its proximal end and a tapered flexible distal portion 73 which provides strain relief. The Luer lock fitting 74 has a female Luer lumen 75 and thread 76. FIG. 7 also shows a longitudinal cross section of the sealing cap 80 in the form of a male Luer lock fitting 81 having threads 82 adapted to screw onto the thread 76 of the guiding catheter's female Luer fitting 74. The conical projection 83 of the male Luer fitting 81 is adapted to mate with the female Luer lumen 75 of the female Luer fitting 74. A hemostasis valve 85 having a slit 86 is of the same general design as the hemostasis valve 37 with slit 34 as shown in FIG. 5. A handle 87 having a conical entry lumen 88 is attached by adhesive bonding, ultrasonic welding, or by any other well known attachment means to the male Luer fitting 81. The handle 87 is a convenient object for the physician to hold as he screws the sealing cap 80 on to and off from the guiding catheter's Luer fitting 74. Also, the conical entry lumen 88 provides an easy access for inserting a guide wire.

As seen in FIGS. 7 and 8, the flexible hinge 90 has a center strap 92 which is joined to torroidal ring 94 on one end and a second torroidal ring 96 at its other end. The ring 94 is adapted to fit around a groove 77 in the fitting 72 and the ring 96 is adapted to fit around a groove 89 that lies between the Luer fitting 81 and the handle 87. Typically, the ring 96 would be continuous but the ring 94 would typically have a slit 95 that allows the sealing cap 80 connected to the flexible hinge 90 to be pulled off the guiding catheter 70 after the sealing cap 80 has served its purpose. It is also envisioned to have slits in either torroidal ring or neither torroidal ring. It is further envisioned that either or both torroidal rings could be rigidly bonded to the guiding catheter 70 or the sealing cap 80.

A typical procedure with the system 60 would be as follows:

(1) The guiding catheter plus sealing cap system 60 would be removed from its sterile package and flushed out with normal saline or a heparin solution.

(2) The sealing cap 80 would be placed over and screwed onto to the female Luer fitting 74 so that the configuration is similar to that shown in FIG. 3. Rotational motion of the sealing cap 80 is made possible because the sealing cap 80 is designed to rotate freely about its longitudinal axis within the torroidal ring 96 of the flexible hinge 90.

(3) A guide wire is placed through the tapered entry cone 88 of the handle 87 and through the lumen 78 of the guiding catheter body 71; the guide wire and guiding catheters are then advanced together through a percutaneous sheath into the arterial system.

(4) The guide wire is then removed and the distal end of the guiding catheter is placed in the ostium of an artery such as a coronary artery.

(5) The sealing cap 80 is unscrewed, a Tuohy-Borst "Y" adaptor is promptly connected to the female Luer fitting 77, and the sealing cap 80 and the flexible hinge 90 are pulled off away from the guiding catheter 70 and discarded.

With the design of the system 60, there are no residual parts remaining on the guiding catheter that could encumber the doctor in his performance of an interventional procedure using the guiding catheter. Another advantage of the system 60 is that different materials, each ideally selected for their function, could be used for the strain relief fitting 72, the flexible hinge 90 the male Luer lock fitting 81 and the sealing cap handle 87.

It should also be understood that the sealing cap 80 could be used separately without any attachment to the guiding catheter 70.

The materials of the guiding catheter 70 are well known in the art. The material of the sealing cap 80 could be polycarbonate, PVC or any similar plastic material. The Luer cap 81 could be made from a different material than the handle 86. The material for the flexible hinge could be any flexible plastic such as polyurethane, Nylon, Teflon, etc.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A guiding catheter with sealing cap system for percutaneous insertion of the guiding catheter into an introducer sheath at the groin and into the femoral artery of a human subject comprising:

a guiding catheter having a proximal end and a distal end and an elongated, generally cylindrical main body, the guiding catheter having a female Luer lumen situated at its proximal end and the distal end being adapted for placement within the ostium of an artery;

a guide wire adapted to be advanced through the guiding catheter and through the arterial system of a human subject; and, a sealing cap having a flexible hinge which is attached to the guiding catheter near its proximal end, the cap further having a tapered stopper which can be releasably inserted into the guiding catheter's female Luer lumen and wherein the sealing cap has a tapered entry cone that is adapted to guide the passage of the guide wire through the stopper when the stopper is inserted into the guiding catheter's female Luer lumen.

2. The system of claim 1 wherein the sealing cap has a central lumen which is adapted to have a sliding fit with the guide wire.

3. The system of claim 1 wherein the sealing cap has a central lumen into which is placed a hemostasis valve which makes elastic contact with the outer surface of the guide wire to prevent the free release of blood.

4. The system of claim 1 wherein the guiding catheter has a female Luer lock fitting at its proximal end and the sealing cap has a male Luer lock fitting adapted to mate with the guiding catheter's female Luer lock fitting, the sealing cap also having a hemostasis valve that allows the passage of a guide wire while preventing the free release of blood.

5. The system of claim I wherein the flexible hinge extends in a generally outward direction from the longitudinal axis of the guiding catheter.

6. The system of claim 1 wherein the flexible hinge is attached to the guiding catheter but can freely rotate about the guiding catheter's longitudinal axis.

7. The system of claim 4 wherein the sealing cap is positioned within a ring on an end of the flexible hinge allowing said sealing cap to freely rotate about its longitudinal axis within said ring.

8. The system of claim 4 wherein the flexible hinge is attached to the guiding catheter by a slit ring at an end of the flexible hinge so that the flexible hinge is easily able to be manually pulled away from the guiding catheter.

9. The system of claim 4 wherein the flexible hinge is attached to the sealing cap by means of a slit ring located at an end of the flexible hinge so that the sealing cap can be manually pulled away from the flexible hinge.

10. A guiding catheter with sealing cap system for percutaneous insertion of the guiding catheter into an introducer sheath inserted at the groin and into the femoral artery of a human subject comprising;

a guiding catheter having a proximal end and a distal end and an elongated, generally cylindrical main body, the guiding catheter having a female Luer lumen situated at its proximal end;

a guide wire adapted to be advanced through the guiding catheter and through the arterial system of a human subject; and, a separate sealing cap having a tapered entry cone so as to provide an entry means for the guide wire, the sealing cap releasably insertable into the guiding catheter's female Luer lumen, the sealing cap further including a blood sealing means that prevents blood leakage while allowing the guide wire to be advanced or pulled back through the blood sealing means of the sealing cap.

11. The system of claim 10 wherein the separate sealing cap is a male Luer lock fitting which can be releasably attached to a female Luer fitting at the guiding catheter's proximal end.

12. The system of claim 10 wherein the separate sealing cap is a "Y" adaptor that has a Tuohy-Borst adjustable seal on one branch of the "Y" and is closed on the other branch of the "Y" adaptor by a second sealing means.

13. The system of claim 12 wherein the Tuohy-Borst adjustable seal of the "Y" adaptor seals around the guide wire and the second sealing means is a closed male Luer cap.

14. The system of claim 12 wherein the second sealing means is a hemostasis valve within a Luer fitting through which the guide wire can be passed while maintaining a pressure seal.

* * * * *